United States Patent  
Hoerger et al.

(10) Patent No.: US 8,038,962 B2  
(45) Date of Patent: Oct. 18, 2011

(54) DEVICE FOR IMPREGNATING A POROUS BONE REPLACEMENT MATERIAL

(75) Inventors: Flavio Hoerger, Biel (CH); Thierry Stoll, Meinisberg (CH)

(73) Assignee: Synthes USA, LLC, West Chester, PA (US)

(*) Notice: Subject to any disclaimer, the term of this patent is extended or adjusted under 35 U.S.C. 154(b) by 1184 days.

(21) Appl. No.: 11/606,506

(22) Filed: Nov. 29, 2006

(65) Prior Publication Data

US 2007/0221742 A1   Sep. 27, 2007

Related U.S. Application Data

(63) Continuation of application No. PCT/CH2004/000335, filed on Jun. 3, 2004.

(51) Int. Cl.
 *B01F 5/00* (2006.01)
(52) U.S. Cl. .................................. 422/263; 366/341
(58) Field of Classification Search .................. 422/263; 366/341; 210/446, 449
 See application file for complete search history.

(56) References Cited

U.S. PATENT DOCUMENTS

| | | | |
|---|---|---|---|
| 2,337,149 A * | 12/1943 | Bullock | 422/263 |
| 4,529,511 A | 7/1985 | Breeden et al. | |
| 4,758,096 A | 7/1988 | Gunnarsson | |
| 4,808,184 A | 2/1989 | Tepic | |
| 4,842,581 A | 6/1989 | Davis | |
| 5,051,482 A | 9/1991 | Tepic | |
| 5,139,031 A | 8/1992 | Guirguis | |
| 5,164,186 A | 11/1992 | Tsuru et al. | |
| 5,181,918 A | 1/1993 | Brandhorst et al. | |
| 5,344,417 A | 9/1994 | Wadsworth, Jr. | |
| 5,425,770 A | 6/1995 | Piez et al. | |
| 5,496,284 A | 3/1996 | Waldenburg | |
| 5,529,463 A | 6/1996 | Layer | |
| 5,531,255 A | 7/1996 | acca | |
| 5,549,380 A | 8/1996 | Lidgren | |
| 5,755,787 A | 5/1998 | Camprasse et al. | |
| 5,772,665 A | 6/1998 | Glad et al. | |
| 5,842,786 A | 12/1998 | Solomon | |
| 5,846,484 A | 12/1998 | Scarborough et al. | |
| 5,876,452 A | 3/1999 | Athanasiou et al. | |

(Continued)

FOREIGN PATENT DOCUMENTS

CA   2419850 AA   2/2002

(Continued)

OTHER PUBLICATIONS

"European Patent Application No. 04750971.6, Communication mailed Jun. 12, 2008", 5 pgs.

(Continued)

*Primary Examiner* — David Sorkin
(74) *Attorney, Agent, or Firm* — Morgan Lewis & Bockius LLP

(57) ABSTRACT

A device for the impregnation of a porous bone replacement material with an impregnation agent includes a container with a central axis and a cavity with a lid. The container has two sealable openings and elastic means. The elastic means are arranged in the cavity allowing a clamping force to be exerted on a bone replacement material inserted in the cavity. A single size container is sufficient for housing variously sized implants, where the implant placed in the cavity of the container is held, centered and protected against damage or breakage, for example, by shaking back and forth or during transportation of the container.

20 Claims, 4 Drawing Sheets

U.S. PATENT DOCUMENTS

| | | | |
|---|---|---|---|
| 6,007,521 | A | 12/1999 | Bidwell |
| 6,027,742 | A | 2/2000 | Lee et al. |
| 6,049,026 | A | 4/2000 | Muschler |
| 6,123,236 | A * | 9/2000 | Bloom .......................... 222/341 |
| 6,143,293 | A | 11/2000 | Weiss et al. |
| 6,383,190 | B1 | 5/2002 | Preissman |
| 6,409,708 | B1 | 6/2002 | Wessman |
| 6,682,347 | B2 | 1/2004 | Aoyagi |
| 6,709,149 | B1 | 3/2004 | Tepic |
| 6,736,799 | B1 | 5/2004 | Erbe et al. |
| 6,796,957 | B2 | 9/2004 | Carpenter |
| 6,887,272 | B2 | 5/2005 | Shinomiya et al. |
| 7,445,633 | B2 | 11/2008 | Hoerger et al. |
| 2004/0226894 | A1 | 11/2004 | Okazaki |
| 2004/0254538 | A1 | 12/2004 | Murphy |
| 2004/0267201 | A1 | 12/2004 | Agerup |
| 2005/0074433 | A1 | 4/2005 | Stoll |
| 2006/0153001 | A1 | 7/2006 | Hoerger et al. |
| 2008/0214998 | A1 | 9/2008 | Kurek |
| 2009/0022878 | A1 | 1/2009 | Hoerger et al. |

FOREIGN PATENT DOCUMENTS

| | | |
|---|---|---|
| CN | 1251046 | 4/2000 |
| DE | 3834944 | 4/1990 |
| DE | 4141129 | 6/1993 |
| EP | 0361896 A2 | 4/1990 |
| EP | 0361896 A3 | 1/1991 |
| EP | 0470393 A1 | 2/1992 |
| EP | 0739631 A2 | 10/1996 |
| EP | 0761896 A1 | 3/1997 |
| EP | 1230942 A2 | 8/2002 |
| FR | 2815021 A1 | 4/2002 |
| JP | 60-142857 | 7/1985 |
| JP | 3-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| JP | 2003010301 | 1/2003 |
| WO | 97/46202 A1 | 12/1997 |
| WO | 9959500 | 11/1999 |
| WO | WO-99/59500 A2 | 11/1999 |
| WO | 00/045867 A1 | 8/2000 |
| WO | WO-01/32100 A2 | 5/2001 |
| WO | 02/15950 A1 | 2/2002 |
| WO | 02/068010 A1 | 9/2002 |
| WO | 2005/014068 A1 | 2/2005 |

OTHER PUBLICATIONS

"International Application Serial No. PCT/CH2004/000335, International Search Report mailed Feb. 9, 2005", (w/ English Translation), 6 pgs.

"International Application Serial No. PCT/CH2004/000335, Written Opinion mailed Feb. 9, 2005", (w/ English Translation), 10 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999),7370-7379.

U.S. Appl. No. 12/242,207, Response filed Nov. 3, 2009 to Non Final Office Action mailed May 4, 2009.

U.S. Appl. No. 12/242,207, Office Action mailed May 4, 2009.

Canada Application Serial No. 2,419,850, Office Action mailed Jul. 7, 2009.

International Patent Application Serial No. PCT/CH01/00494, International Preliminary Examination Report dated Aug. 26, 2002, (w/ English Translation).

International Patent Application Serial No. PCT/CH01/00494, International Search Report mailed Dec. 5, 2001, (w/ English Translation).

International Search Report for Application No. PCT/CH03/00537, date mailed Apr. 16, 2004.

U.S. Appl. No. 11/349,693, Response filed Jun. 16, 2008 to Final Office Action mailed Mar. 17, 2008.

U.S. Appl. No. 11/349,693, Notice of Allowance mailed Jun. 30, 2008, NOAR.

Application U.S. Appl. No. 11/349,693, Final Office Action mailed Mar. 17, 2008, FOAR.

International Search Report for International Application No. PCT/CH03/00537.

U.S. Appl. No. 11/349,693, Non-Final Office Action Mailed Sep. 7, 2007.

U.S. Appl. No. 11/349,693, Response filed Dec. 7, 2007 to Office Action mailed Sep. 7, 2007.

Merriam-Webster MedLine Plus Online Medical Dictionary definitions of "vacuum," "membrane," and "septum." Accessed online at <http://www.nlm.nih.gov/medlineplus/mplusdictionary.html> on Oct. 16, 2008.

Definition of "membrane." The American Heritage Dictionary of the English Language, Fourth Edition Copyright 2007, 2000 by Houghton Mifflin Company. Updated in 2007.

"Body." in: Costell, RB, ed., Random House Webster's College Dictionary (1991 ed.), p. 152.

Medline Plus Medical Dictionary Definition of "osteogenic." Accessed online Dec. 12, 2005.

Dictionaly.com definition of "mesenchymal." Accessed online Dec. 12, 2005.

EPOline Online Public File Inspection entry for WIPO document WO2000CH00443, accessed online Dec. 13, 2005.

Linkart TA et al., 1996, Growth factors for bone growth and repair: IGF; TGF beta, and BMP. Bone 19 (1 Suppl):1S-12S. Abstract only.

U.S. Appl. No. 10/370,606, Non-Final Office Action mailed Dec. 19, 2005.

U.S. Appl. No. 10/370,606, Final Office Action mailed May 31, 2006.

U.S. Appl. No. 10/370,606, Non-Final Office Action mailed Dec. 18, 2006.

U.S. Appl. No. 10/370,606, Final Office Action mailed Jun. 15, 2007.

U.S. Appl. No. 10/370,606, Non-Final Office Action mailed Dec. 11, 2007.

U.S. Appl. No. 10/370,606, Final Office Action mailed May 1, 2008.

U.S. Appl. No. 10/370,606, Non-Final Office Action mailed Oct. 31, 2008.

U.S. Appl. No. 10/370,606, Final Office Action mailed May 21, 2009.

U.S. Appl. No. 10/370,606, Non-Final Office Action mailed Dec. 16, 2009.

U.S. Appl. No. 10/370,606, Final Office Action mailed Jun. 3, 2010.

Barry T. Mitzner, Hematology Methods for the Office Laboratory Power Point Presentation, Jun. 12, 1999.

"International Application Ser. No. PCT/US06/41202, International Preliminary Report Patentability mailed on Sep. 3, 2008," 10 pages.

"International Application No. PCT/US06/41202, International Search Report mailed on Sep. 26, 2007," 3 pages.

"International Application No. PCT/US06/41202, Written Opinion mailed on Sep. 26, 2007," 7 pages.

Stile, R.A., et al., "Synthesis and Characterization of Injectable Poly(N-isopropylacrylamide)-Based Hydrogels That Support Tissue Formation in Vitro", Macromolecules, 32, (1999), 7370-7379.

U.S. Appl. No. 12/089,679, Final Office Action mailed Jul. 13, 2010.

U.S. Appl. No. 12/089,679, Non-Final Office Action mailed Dec. 24, 2009.

Taiwan patent application No. 94113414, English Translation of an Office action dated Jul. 22, 2011 (5 pages).

Taiwan patent application No. 94113414, Taiwanese version of the Office action dated Jul. 22, 2011 (12 pages).

* cited by examiner

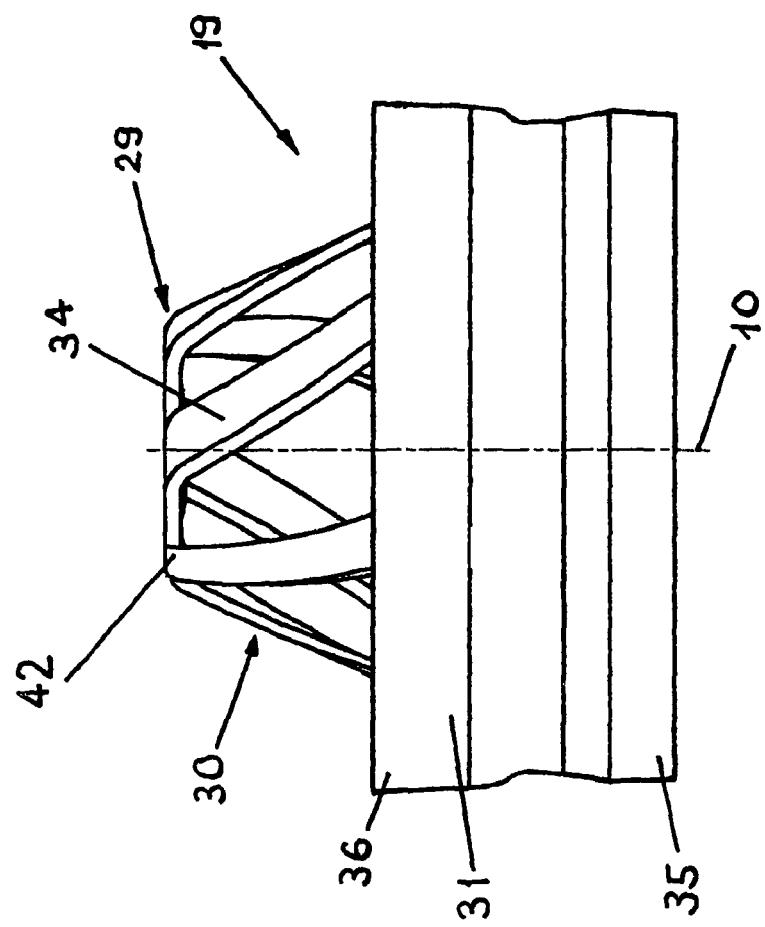
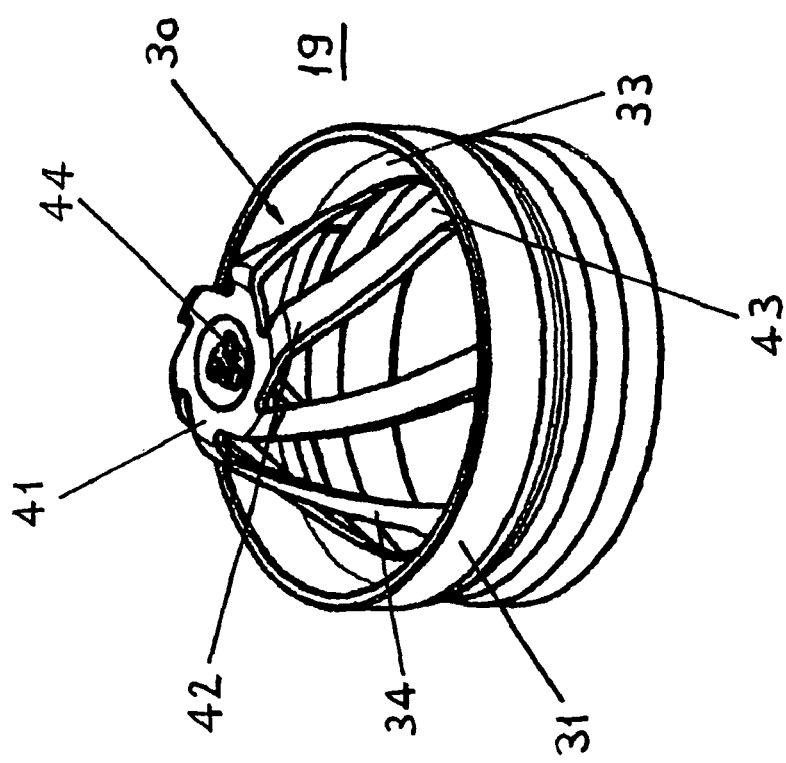
Fig. 3
Fig. 4

US 8,038,962 B2

DEVICE FOR IMPREGNATING A POROUS BONE REPLACEMENT MATERIAL

CROSS REFERENCE TO RELATED APPLICATION

This application is a continuation of International Patent Application No. PCT/CH2004/000335, filed on Jun. 3, 2004, the entire contents of which is expressly incorporated herein by reference.

TECHNICAL FIELD

The invention refers to a device for impregnating a porous bone replacement material.

BACKGROUND OF THE INVENTION

A device for impregnating a porous, biocompatible bone replacement material is already known from U.S. Pat. No. 6,049,026 to MUSCHLER. This known device comprises a chamber for receiving the bone replacement body as well as a first container above the chamber, for storing an impregnation agent and a second container below the chamber for receiving the impregnation agent flowing through the chamber with the bone replacement body. When opening a first valve set between the first container and the chamber, the impregnation agent flows into the chamber with the bone replacement body. As soon as the chamber is filled, a second valve set between the chamber and the second container opens, so that the impregnation agent can flow into the second container through a membrane arranged below the bone replacement body. A disadvantage of this known device is that the bone replacement body in the chamber cannot be clamped down in the chamber, so that the bone replacement material or implant can, for instance by shaking back and forth during transport, be damaged or broken.

SUMMARY OF THE INVENTION

The present invention provides a remedy for the above-discussed disadvantage. It is an object of the invention to produce or create a device for impregnating a porous bone replacement material whereby an implant, for example, a body made of bone replacement material, can be secured against damage by shaking back and forth, for instance during transport.

In a preferred embodiment the device for impregnating a porous bone replacement material has a container, having a central axis, including a cavity and a lid. The container is included with two openings fitted with a lock, and comprises elastic means arranged inside the cavity, whereby a bone replacement material introduced into the cavity is subjected to a clamping force. Advantages gained by the device acc are:

a single container size suffices for receiving variously sized implants in the same, and an implant inserted into the cavity of the container is firmly held, centered and protected, for instance against shaking back and forth or while transporting the container.

The elastic means may preferably be conformed like a bellows or a spring. The elastic means may also comprise a spring element set up coaxially to the central axis encompassing elastic webs set up in a helical or coaxial form with respect to the central axis. The configuration of the spring element fitted with such webs allows an application of large through opening passages for the impregnation agent, so as to generate a low resistance while flowing through the spring element.

Further advantages are in the fact that the holding force on the implant is uniform and centers the implant. The webs may exhibit upper ends turned toward the cover, which open out in a central plate set up concentrically to the central axis and fitted with perforations, whose diameter measured in a direction orthogonal to the central axis d may measure between about 0.001% and 99.999% and preferably between about 0.1% and 99.9% of the cavity diameter D measured orthogonally to the central axis. The diameter d may be between about 1% and 99%, and preferably between about 5% and 95% of the diameter D. The diameter d is typically between about 10% and 90%, and preferably between about 20% and 80% of the diameter D. The diameter d is advantageously between about 25% and 75%, and preferably between about 30% and 40% of the diameter D. The small diameter of the central plate with respect to that of the cavity allows only a small portion of the implant surface not to be exposed to the impregnation agent. A further advantage is that the holding force on the implant is uniform and that the implant is also centered.

In another embodiment, the webs may have lower ends opening out into an outer ring of the spring element. The outer ring may in this case be seated in the cavity. After the cover is screwed tight, the elastic means are thus fastened by the spring element pressing against the cover and by being seated in the cavity. Other advantages are based on the fact that the shape of the seal may prevent it from tilting off from the axis and that the dead space of the lower external ring is reduced, so that less blood is needed for a perfusion.

In an additional embodiment, a gasket may be provided between the container and the lid. This allows the container to shut tightly even under a vacuum condition. In another embodiment, the spring element and the gasket may be formed in a single piece. This results in a simple assembly of the device and prevents a loss of the gasket.

In a further embodiment, the cavity height H is measured parallel to the central axis is defined by the external ring and the gasket height is measured parallel to the central axis. This makes it possible to apply for instance gaskets or spring elements of different size to define the height of the cavity. A further advantage lies in the reduced production and packing costs, because only a single container may be employed for a multiple number of variously sized implants.

The height measured parallel to the central axis may alternatively be defined by inner parts of different height, preferably through the lid.

In still another embodiment, the elastic means exhibit—if measured parallel to the central axis and in an unloaded condition—a height h and are axially compressible by a measure $\Delta h$, where the ratio $\Delta h:h$ lies between about 0.001% and 99.999%, and preferably between about 0.01% and 99.99%. The ratio of $\Delta h: h$ may typically be between about 0.1% and 99.9%, and preferably between about 1% and 99%. The ratio of $\Delta h:h$ is advantageously between about 5% and 95%, and preferably between about 10% and 90%. The elastic means are thus compressible to a high degree, so that variously sized implants can be accommodated.

In a further embodiment, the container is shaped like a cylinder and presents a coaxially arranged inner thread, while the lid comprises an outer thread complementary to the inner thread.

The container advantageously contains a porous bone replacement material, whose overall volume v is smaller than the volume V of the cavity. The bone replacement material may be available in the form of a block, preferably in the form of a cube, cylinder, hollow cylinder, disc, wedge, cone, truncated cone or a ball. The bone replacement material may be fitted inside an implant so as to communicate at least partially with the surface of the implant itself.

The implant may be chosen from one or more of the following groups of materials: metal, synthetic material, nonmetal, preferably glass, ceramics of different density, and composite ceramics.

The elastic means may be set up symmetrically or asymmetrically to the central axis. Depending on the configuration or form of the implant, an either symmetrical or asymmetrical construction may offer a better support for the implant.

The container bottom may be fitted with a centrally or de-centrally perforated connecting piece forming one of the two openings. A centrally or de-centrally perforated connecting piece can also be set up on the lid cover over one of the two opening.

An impregnation agent may comprise osteoinductive and/or osteogenic substances, in particular bone cells, bone marrow or bone marrow components, blood or blood components or a combination thereof.

A method for impregnating a porous bone replacement material with an impregnation agent comprising the steps of injecting the impregnation agent using a syringe having a piston. Preferably the syringe is connected to at least one of a lower opening and upper opening of a container so that a block made of porous bone replacement material is surrounded by the impregnation agent and is at least partially submerged in the same. Both openings may be formed as Luer openings with a conically perforated connecting piece connected to the container. Withdrawing the piston of the syringe, so as to create a vacuum in the container, causes the air present in the pores of the bone replacement material to expand so as to move out of the pores and into the surrounding impregnation agent. Because of the closed system the piston motion aspirates the impregnation agent only partially. Pressing the piston of the syringe again into the original position eliminates the vacuum in the container.

BRIEF DESCRIPTION OF THE DRAWINGS

The device is explained in even greater detail in the following exemplary drawings. The device may be better understood by reference to the following drawings, wherein like reference numerals represent like elements. The drawings are merely exemplary to illustrate structure, operation and method of use of the device and certain features that may be used singularly or in combination with other features, and the invention should not be limited to the embodiments shown.

FIG. 3 is a perspective view of an elastic means as part of the device shown in FIG. 1 and 2;

FIG. 4 is a sectional view of the elastic means shown in FIG. 3;

DESCRIPTION OF THE PREFERRED EMBODIMENTS

Figure 1:
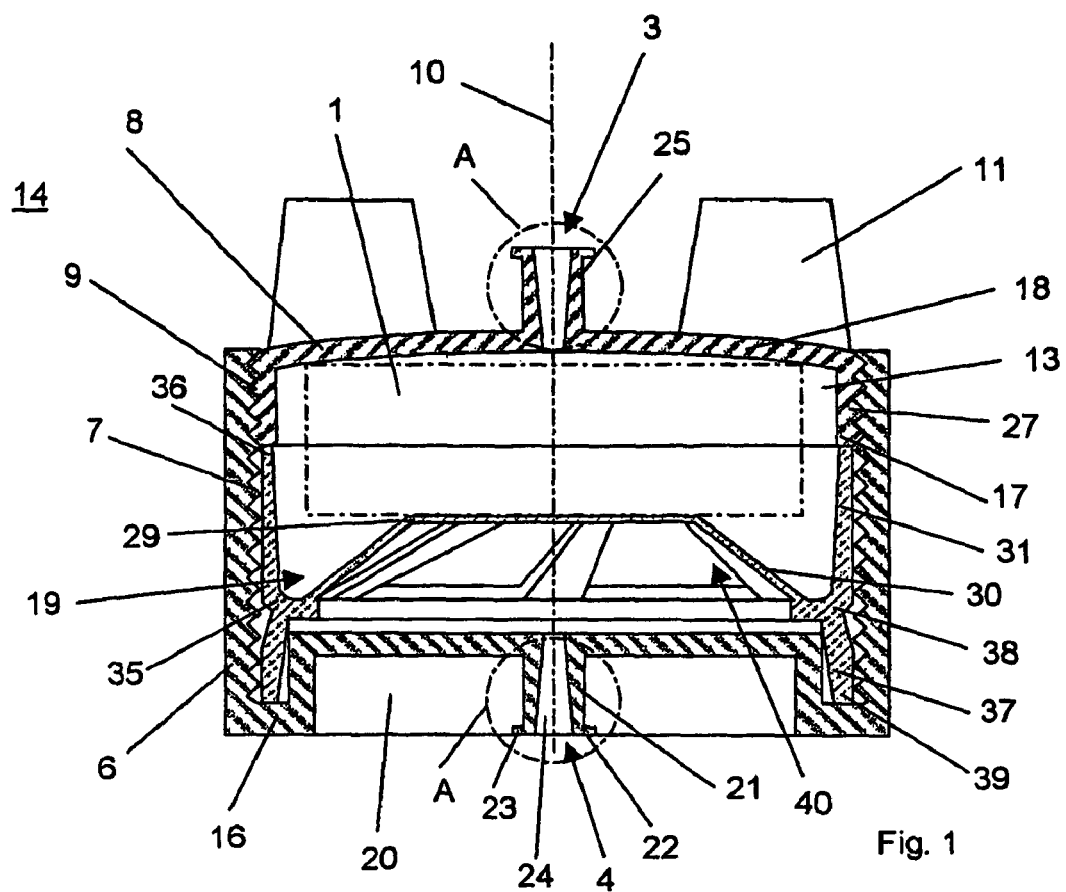
FIG. 1 is a cross-section of an embodiment of the device according to the invention.

FIG. 1 shows an embodiment of the device 14 which comprises a cylindrical container 6 set up coaxially to the central axis 10 and fitted with a lid 8 that is fastenable onto container 6. The container 6 may have a cavity 13, an inner thread 7 set up coaxially to the central axis 10 so that the lid 8, which has on its outer mantle surface 27 an outer thread 9 complementary to the inner thread 7, may be connected to the container 6 in a detachable manner. The inner thread 7 may extend over the entire axial length of the cavity 13 in the container 6. Alternatively, a multiple thread extending only up to half of the container 6 may be employed. The outer thread 9 on the lateral mantle surface 27 of the lid 8 may extend over the entire axial length of the lid 8. The elastic means 19, which may comprise in one embodiment an axial elastic spring element 30 and a hollow cylinder gasket 31 which may be formed in a single unit, is arranged inside the cavity 13.

The hollow cylinder gasket 31 may extend parallel to the central axis 10 between upper end 38 of outer ring 37 which is part of the spring element 30 and lower end 17 of the lid 8. The lower end 39 of the outer ring 37 rests on bottom 16 of the container 6, while the upper end 38 of the outer ring 37 is connected to lower end 35 of the gasket 31. The outer ring 37 may be formed with an outer diameter adapted to the inner diameter of the container 6, so as to secure the elastic means 19 against shifting in a direction transverse to the central axis 10.

The lid 8 may be threaded into the cavity 13 of the container 6, until the lower end 17 of the lid 8 rests on the upper end 36 of the gasket 31. The inner thread 7 as well as the outer thread 9 may be formed as multiple threads. The bottom 16 of the container 6 is fitted with a depression 20 concentric to a central axis 10, where a centrally perforated connecting piece 21 is set up concentric to the central axis 10. Central perforation 24 of the connecting piece 21 forms opening 4. Analogous to this, a second connecting piece 25 perforated concentrically to the central axis 10 is set up outside the cover plate 18 of the lid 8. The connecting pieces 21 and 25 may be formed in an identical manner. The two connecting pieces 21 and 25 alternatively may be formed in a different manner.

When screwing the lid 8 into the container 6, a piece of bone replacement material 1 inserted into the cavity 13 of the container 6 is pressed against the upper end 29 of the spring element 30 so that the spring element 30 is compressed by a measure Δh. Owing to the elasticity of the spring element 30, the body of the bone replacement material 1 is clamped between the upper end 29 of the spring element 30 and cover plate 18 of the lid 8. The bone replacement material is accommodated inside an implant in such a way that it communicates with the surface of the implant at least in part.

FIGS. 3 and 4 represent an embodiment of the elastic means 19, which may consist of a spring element 30 with an outer ring 37 and a truncated-cone type segment arranged at the upper end 38 of the outer ring 37. This truncated cone type segment 40 comprises webs 34, whose upper ends 42 open up into a central plate 41 which is arranged concentrically to the central axis 10 at the upper end 29 of the spring element 30 and fitted with perforations 44, and whose lower ends 43 are connected to the outer ring 37 at element 33. The truncated cone type segment 40 is conformed in a tapered manner toward the upper end 29 of the spring element 30, while the webs 34 are spirally arranged around the central axis 10.

Figure 2:
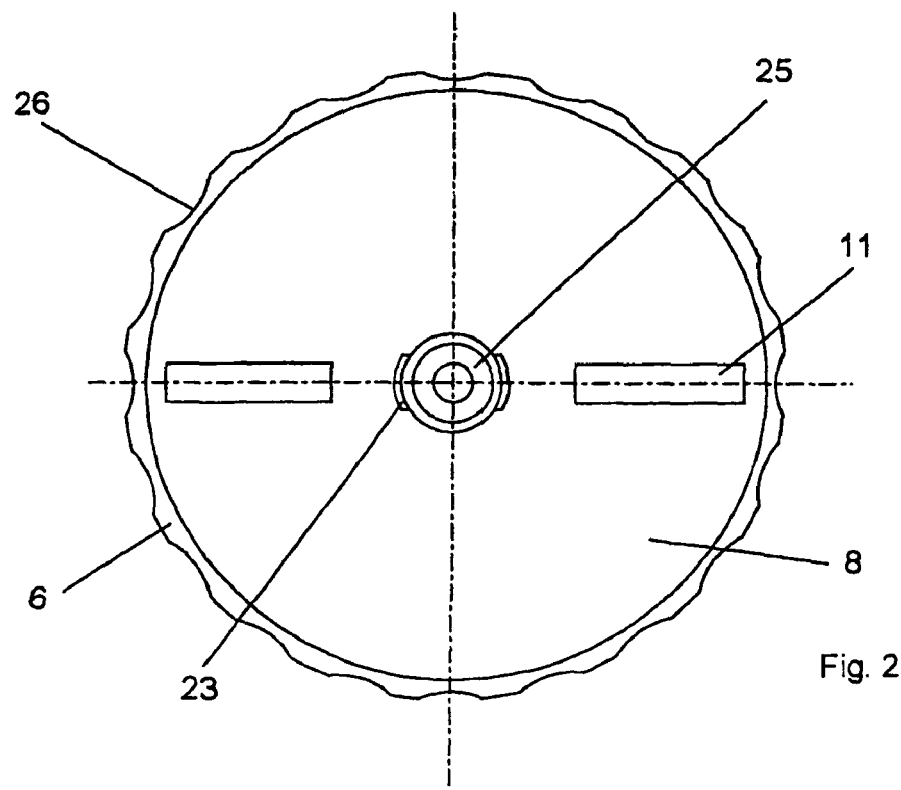
FIG. 2 is a topside view of the device shown in FIG. 1.
Figure 5:
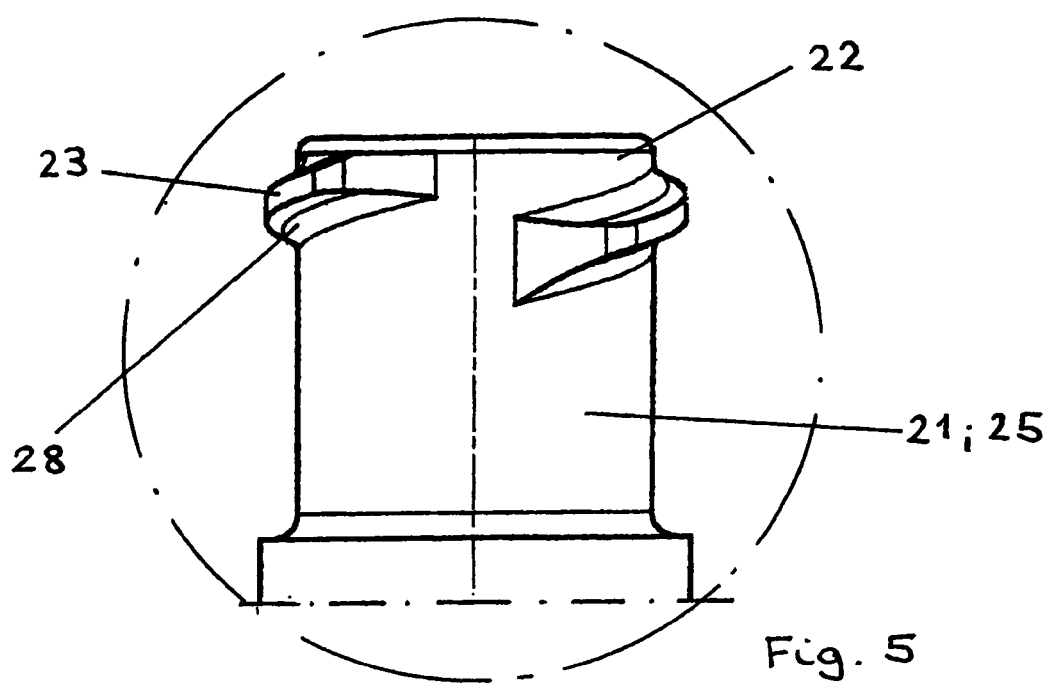
FIG. 5 is a view of the connecting piece marked off by the circle A in FIG. 1.
Figure 6:
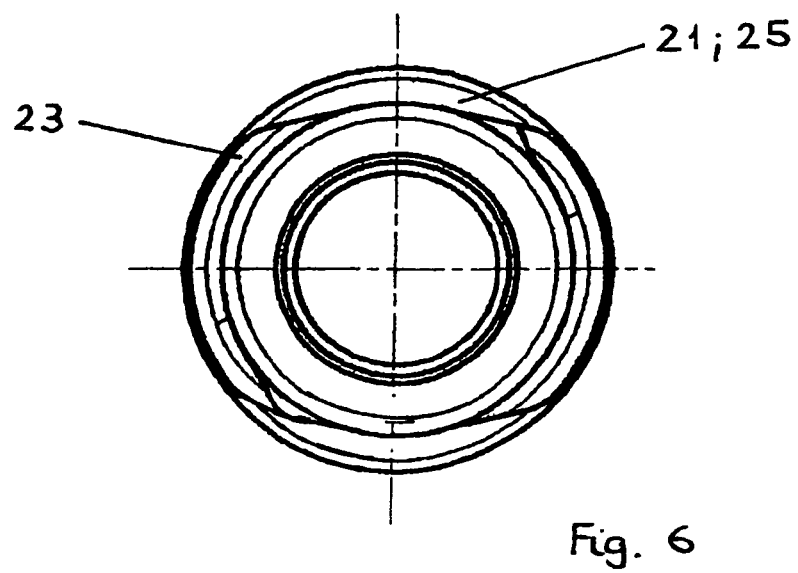
FIG. 6 is a topside view of the connecting piece shown in FIG. 5.

FIGS. 5 and 6 illustrate the connecting pieces 21, 25, which are identically confirmed as male Luer connecting pieces. Each of the connecting pieces 21, 25 comprises at its free end 22 two radially projecting cams 23, which are formed by two pairs of diametrically opposed segments of a thread 28, respectively. A standard injector 15 (FIG. 7) conformed as a complementary female Luer connecting piece at its opening toward the connecting piece 21 may be screwed on over each of the connecting pieces 21, 25 (Luer connecting piece). The connecting pieces can be chosen so that different adapters may be connected to the same in an airtight fashion. Arranging (FIG. 1) the connecting piece 21 in depression 20 so that the connecting piece 21 cannot project above the bottom 16 of the container 20, the container 6 can be laid on the floor without tilting over. To facilitate threading the lid 8 into or onto the container, two axially projecting rises 11 are provided on the outer side of the cover plate 18 on the lid 8, and two axially running grooves 26 are provided on the outer mantle surface of the container 6 (FIG. 2).

The elastic means 19 may preferably be configured like bellows or a spring. The elastic means 19 may also comprise a spring element set up coaxially to the central axis 10 encompassing elastic webs set up in a helical or coaxial form with respect to the central axis. The configuration of the spring element fitted with such webs allows an application of large through opening passages for the impregnation agent 5, so as to generate a low resistance while flowing through the spring element. Further advantages are in the fact that the holding force on the implant is uniform and centers the implant. The webs may exhibit upper ends turned toward the cover, which open out in a central plate set up concentrically to the central axis and fitted with perforations, whose diameter measured in a direction orthogonal to the central axis d may measure between about 0.001% and 99.999% and preferably between about 0.1% and 99.9% of the cavity diameter D measured orthogonally to the central axis. The diameter d may be between about 1% and 99%, and preferably between about 5% and 95% of the diameter D. The diameter d is typically between about 10% and 90%, and preferably between about 20% and 80% of the diameter D. The diameter d is advantageously between about 25% and 75%, and preferably between about 30% and 40% of the diameter D. The small diameter of the central plate with respect to that of the cavity allows only a small portion of the implant surface not to be exposed to the impregnation agent. A further advantage is that the holding force on the implant is uniform and that the implant is also centered.

In another embodiment, the webs 34 may have lower ends opening out into an outer ring of the spring element. The outer ring 37 may in this case be seated in the cavity free of play. After the cover is screwed tight, the elastic means are thus fastened by the spring element pressing against the cover and free from any play in the cavity. Other advantages are based on the fact that the shape of the seal will prevent it from tilting off of the axis and that the dead space of the lower external ring is reduced, so that less blood is needed for the perfusion.

In an additional embodiment, a gasket 31 may be provided between the container 6 and the lid 8. This allows the container 6 to shut tightly even under a vacuum condition. In another embodiment, the spring element 30 and the gasket 31 may be formed in a single piece. This results in a simple assembly of the device and prevents a loss of the gasket.

In a further embodiment, the cavity 13 height H is measured parallel to the central axis defined by the external ring and the gasket height is measured parallel to the central axis 10. This makes it possible to apply for instance gaskets or spring elements of different size to define the height of the cavity.

The height measured parallel to the central axis may alternatively be defined by inner parts of different height, preferably through the lid.

In still another embodiment, the elastic means 19 exhibit—if measured parallel to the central axis 10 and in an unloaded condition—a height h and are axially compressible by a measure Δh, where the ratio Δh:h lies between about 0.001% and 99.999%, and preferably between about 0.01% and 99.99%.

The ratio of Δh:h may typically be between about 0.1% and 99.9%, and preferably between about 1% and 99%. The ratio of Δh:h is advantageously between about 5% and 95%, and preferably between about 10% and 90%. The elastic means are thus compressible to a high degree, so that variously sized implants can be accommodated.

In a further embodiment, the container 6 is shaped like a cylinder and presents a coaxially arranged inner thread, while the lid comprises an outer thread complementary to the inner thread.

The container 6 advantageously contains a porous bone replacement material, whose overall volume v is smaller than the volume V of the cavity. The bone replacement material may be available in the form of a block, preferably in the form of a cube, cylinder, hollow cylinder, disc, wedge, cone, truncated cone or a ball. The bone replacement material may be fitted inside an implant so as to communicate at least partially with the surface of the implant itself.

The implant may be chosen from one or more of the following groups of materials: metal, synthetic material, non-metal, preferably glass, ceramics of different density, and composite ceramics.

The elastic means may be set up symmetrically or asymmetrically to the central axis. Depending on the configuration or form of the implant, an either symmetrical or asymmetrical construction offers a better support for the implant.

The container bottom may be fitted with a centrally or de-centrally perforated connecting piece forming one of the two openings. A centrally or de-centrally perforated connecting piece can also be set up on the lid cover over one of the two opening.

The impregnation agent 5 may comprise osteoinductive and/or osteogenic substances, in particular bone cells, bone marrow or bone marrow components, blood or blood components or a combination thereof.

Figure 7:
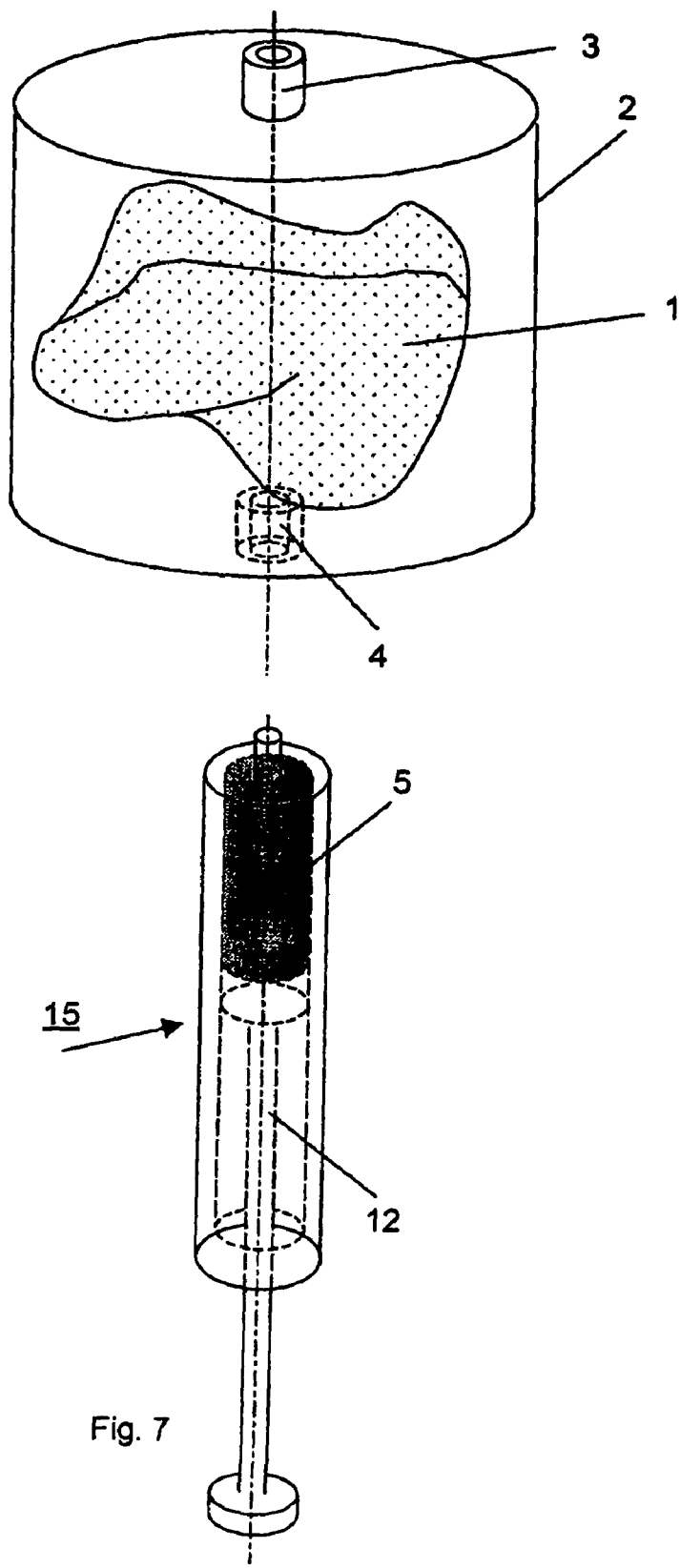
FIG. 7 is a perspective view of an embodiment of the device and of a syringe.

FIG. 7 shows a container 6 with a body composed of a bone replacement material 1 enclosed in the cavity surrounded by outer wall 2. The container 6 has two openings 3, 4, which may be airtight connected by a syringe 15. The syringe may in its cavity contain osteoinductive and/or osteogenic substances, in particular body cells, bone marrow and/or bone marrow elements, blood and/or other blood elements as an impregnation agent 5. The container 6 illustrated in this case, together with the syringe 15, serves to perform the following process:

A) A syringe 15 filled with impregnation agent 5 is preferably connected to the lower opening or both openings 4 of the container 6. The upper opening 3 remains open. Both openings 3, 4 are configured as Luer openings with a conically perforated connecting piece 21, 25 connected to the container 6 (FIGS. 5 and 6). The impregnation agent 5 is injected by the piston 12 through the opening 4 into the container 6, so that the block made of porous bone replacement material 1 is surrounded by the impregnation agent 5 and is partially or preferably wholly submerged in the same;

B) The upper opening 3 is now closed;

C) The piston 12 of the syringe 5 is then again withdrawn, so as to create a negative pressure or vacuum in the container 6. Because of the vacuum, the air present in the pores of the bone replacement material 1 is induced to expand, so as to move out of the pores and into the surrounding impregnation agent 5. Because this is a closed system, the piston motion aspirates the impregnation agent 5 only partially. This is also possible only if the container 6 still contains air. In addition, a large volume of impregnation agent 5 also exhibits adhering characteristics and thus adheres to the surface of the bone replacement material 1, without being aspirated by the piston motion;

D) In a next step, the piston 12 of the syringe 5 is pressed again into the original position, so as to eliminate the vacuum in the container 6. The block of bone replacement material 1 surrounded by the impregnation agent 5 now absorbs into its pores only impregnation agent 5, and not air, so that an impregnation of the bone replacement material 1 will occur. The evacuation/elimination of the vacuum drawn with the syringe 5 in the container can be repeated several times to boost the degree of impregnation. Because of its adhesion property and the capillary effect of the structure of the porous bone replacement material 1, the impregnation agent 5 typically is better absorbed into its interior than air.

Another embodiment of the process lies in the fact that after coupling the first syringe 15 filled with impregnation agent 5 to one of the two openings 3, 4, the second, unfilled syringe (not shown) is coupled to the other opening 3, 4, and the cavity of the container 6 is evacuated by withdrawing the piston and at the same time aspirating the impregnation agent 5, through the resulting negative pressure, from the cavity in the syringe 15 into the cavity of the container 6. The air in the pores of the bone replacement material 1 escapes from the pores. By pressing in the piston of the second syringe, the air is subsequently moved again into the container 6, so that the vacuum in the cavity of the container 6 is again eliminated and the impregnation agent 5 can penetrate into the pores of the bone replacement material.

If necessary the piston of one of the syringes can be withdrawn and the container can be evacuated again. The process steps of evacuating and eliminating the vacuum can be simply repeated in this manner, until the pores in the bone replacement material 1 are adequately de-aerated and filled with impregnation agent 5.

Another embodiment of the process consists in the fact that the second syringe (not shown) is applied to increase the vacuum. This second syringe can—because it is not filled with impregnation agent 5—present a considerably greater volume than the first syringe 15 filled with impregnation agent 5.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A device for impregnating a porous bone replacement material with an impregnation agent comprising:
a container, having a central axis, a cavity, a lid, and two openings fitted with a closure,
wherein the device comprises elastic means arranged inside the cavity and a gasket radially disposed about the central axis and connected to the elastic means, whereby a bone replacement material introduced into the cavity is subjected to a clamping force.

2. A device according to claim 1, wherein the elastic means are conformed as bellows or a spring.

3. A device according to claim 1, wherein the elastic means comprises a spring element coaxially arranged with respect to the central axis and having a plurality of elastic webs which are helically or spirally disposed about the central axis.

4. A device according to claim 3, wherein the plurality of elastic webs have upper ends turned toward the lid, which open up to a central plate fitted with perforations and arranged concentrically to the central axis, the lid's diameter d measured orthogonally to the central axis amounts to between about 0.001% and about 99.999% of the diameter D of the cavity, measured orthogonally to the central axis of the cavity.

5. A device according to claim 4, wherein the diameter d is between about 10% and about 90% of the diameter D.

6. A device according to claim 4 wherein the diameter d is between about 25% and about 75% of the diameter D.

7. A device according to claim 3, wherein the webs include lower ends which open up into an outer ring of the spring element.

8. A device according to claim 1, wherein the gasket engages the lid.

9. A device according to claim 3, wherein the spring element and the gasket are formed in a single piece.

10. A device according to claim 8, wherein a height H of the cavity measured parallel to the central axis is defined by a height of an outer ring measured parallel to the central axis and by the gasket.

11. A device according to claim 8, wherein a height H of the cavity measured parallel to the central axis is defined by internal elements of various heights, including the lid.

12. A device according to claim 1, wherein the elastic means has in an unloaded condition a height h measured parallel to the central axis and is compressible in an axial direction by a measure $\Delta h$, and wherein a ratio $\Delta h$:h is between about 0.001% and about 99.999%.

13. A device according to claim 12, wherein the ratio $\Delta h$:h is between about 5% and about 95%.

14. A device according to claim 1, wherein the bone replacement material is accommodated inside an implant in such a way that it communicates with a surface of the implant at least in part.

15. A device according to claim 1, wherein the elastic means is arranged symmetrically to the central axis.

16. A device according to claim 1, wherein the elastic means is arranged asymmetrically to the central axis.

17. A device according to claim 1, wherein a bottom of the container is fitted with a centrally perforated connecting piece which forms one of the two openings.

18. A device according to claim 1, wherein a bottom of the container is fitted with a perforated connecting piece which forms one of the two openings, the perforation is not centrally located.

19. A device according to claim 1, wherein a centrally perforated connecting piece, which forms one of the two openings, is arranged on an outside surface of a cover plate of the lid.

20. A device according to claim 1, wherein a perforated connecting piece having a perforation that is not centrally located, forms one of the two openings, is arranged on an outside surface of a cover plate of the lid.

* * * * *

UNITED STATES PATENT AND TRADEMARK OFFICE
CERTIFICATE OF CORRECTION

| | | |
|---|---|---|
| PATENT NO. | : 8,038,962 B2 | Page 1 of 1 |
| APPLICATION NO. | : 11/606506 | |
| DATED | : October 18, 2011 | |
| INVENTOR(S) | : Hoerger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1245 days.

Signed and Sealed this
Sixth Day of March, 2012

David J. Kappos
*Director of the United States Patent and Trademark Office*